United States Patent [19]

Neubardt

[11] Patent Number: 4,936,319
[45] Date of Patent: Jun. 26, 1990

[54] SURGICAL TOWEL AND PROCEDURE FOR AVOIDING HYPOTHERMIA

[76] Inventor: Seth Neubardt, 240 E. 76th St., 190 14U, New York, N.Y. 10021

[21] Appl. No.: 403,470

[22] Filed: Sep. 6, 1989

[51] Int. Cl.$^5$ .............................................. A61F 7/12
[52] U.S. Cl. .................................. 128/849; 128/401; 128/155
[58] Field of Search ................... 128/849–850, 128/155–156, 399–403

[56] References Cited

U.S. PATENT DOCUMENTS

| | | | |
|---|---|---|---|
| 3,867,939 | 2/1975 | Moore et al. | 128/400 |
| 4,349,020 | 9/1982 | Krikorian . | |
| 4,397,315 | 8/1983 | Patel . | |
| 4,413,624 | 11/1983 | Snow | 128/399 |
| 4,534,354 | 8/1985 | Bonner, Jr. et al. . | |
| 4,605,006 | 8/1986 | Jacques | 128/403 |
| 4,618,524 | 10/1986 | Groitzsch et al. . | |
| 4,649,909 | 3/1987 | Thompson . | |
| 4,715,366 | 12/1987 | Teeple | 128/849 |
| 4,765,323 | 8/1988 | Poettgen | 128/156 |
| 4,781,962 | 11/1988 | Zamarripa et al. . | |

OTHER PUBLICATIONS

"Unintentional Hypothermia in the Operating Room: a Footnote", 35 Canadian J. of Anaesthesia, pp. 206–208 (1988).
"Inadvertent Hypothermia", 10 Today's OR Nurse, pp. 27–32 (Jul., 1988).
"Inadvertent Hypothermia", 44 AORN Journal, pp. 54–61 (Jul., 1986).

Primary Examiner—Robert A. Hafer
Assistant Examiner—Kerry Owens
Attorney, Agent, or Firm—Leo Zucker

[57] ABSTRACT

A surgical towel useful for preventing unintentional hypothermia induced by a prolonged surgical procedure. The towel includes a body heat retaining layer portion of thermally insulative flexible material, and a soft absorbent covering layer portion which is adhered to the outside major surfaces of the heat retaining layer portion. The covering and the heat retaining layer portions together are capable of being wrapped or draped about an exposed organ to prevent loss of body heat through the organ while surgery is in progress.

5 Claims, 4 Drawing Sheets

SURGICAL TOWEL AND PROCEDURE FOR AVOIDING HYPOTHERMIA

BACKGROUND OF THE INVENTION

1. Field of the Invention.

The present invention relates generally to surgical towels and drapes, and particularly to a towel or drape useful in avoiding loss of a patient's core body heat as a result of a prolonged operation.

2. Discussion of the Known Art.

Hypothermia, i.e., a drop in core body temperature below 36° C. (96.8° F.), has been known to occur in patients who have undergone extensive or prolonged surgery. Referred to as accidental, inadvertent, unintentional, intraoperative or perioperative hypothermia, the occurrence of this type of hypothermia is recognized in the medical field as a serious problem, giving rise to complications such as shivering, vasoconstriction and cardiovascular instability, particularly in older patients. For example, see M. D. Fallacaro, et al, Inadvertent Hypothermia, 44 ARON Journal (No. 1) at 54, et seq. (July 1986); and N. L. Burkle, Inadvertent Hypothermia, 10 Today's OR Nurse (No. 7) at 27, et seq. (July 1988).

There are several causes of unintentional hypothermia. Modern operating theatres are closely temperature controlled for the comfort of the surgeons and attendants. Typical operating room temperatures are maintained below 20° C. (68° F.), regardless of the number of hours extensive surgery may be carried out. The ambient temperature is therefore 16 degrees C. below the patient's core level. Because of this temperature imbalance, heat is lost from the patient's body by radiation through the open incision into the surrounding environs.

Further, the common practice of applying wet cotton towels on exposed organs and other areas of the surgical field, actually tends to promote body cooling by evaporation. That is, even moist heated towels will become cold by evaporative cooling.

Once unintentional hypothermia is diagnosed, it becomes very difficult to reverse the body cooling trend. Current methods of treating or preventing hypothermia have substantially failed to prevent further heat loss. Such methods include the following:

1. Raising the operating room temperature.
2. Using portable radiant heating lamps.
3. Use of warm blankets.
4. Warming the patient mattress.
5. Reflective blankets.
6. Heated gases.
7. Blood warmers.
8. Fluid warmers.
9. Irrigation with warm fluids.

In major abdominal surgical procedures, much serous viscera become exposed to the operating room environs and wetted cold towels. This condition is one in which evaporative heat loss becomes at least as great a factor that contributes to overall body heat loss, as does any radiative heat loss through the opened abdominal cavity. The various active patient warming techniques noted above therefore must overcome the combined radiative and evaporative heat losses if they are to avoid hypothermia resulting from protracted abdominal surgery.

A material sold under the name "Space Blanket" has been experimented with as a means of avoiding hypothermia in patients undergoing neurosurgery. See P. Radford, et al, Metallized Plastic Sheeting in the Prevention of Hypothermia During Neurosurgery, 51 Br. J. Anaesthesia 237 (1979); and J. Brunton, et al, Reduction of Heat Loss in Neurosurgical Patients Using Metallized Plastic Sheeting, 54 Br. J. Anaesthesia 1201 (1982).

Each "Space Blanket" consists of an artificial fibre layer with two outside layers of metallized plastics sheeting (m.p.s.). In the experiments, patients were wrapped with m.p.s. prior to surgery, but the immediate surgical field was left exposed. The reported results showed that as used, m.p.s. alone was not sufficient to maintain normal body temperature during surgery, and that active warming systems were needed to ensure normothermia.

SUMMARY OF THE INVENTION

An object of the invention is to overcome the shortcomings of the known techniques for maintaining a surgical patient's core body temperature at a normal level, particularly during and after a protracted operating procedure.

Another object of the invention is to provide a technique for avoiding accidental hypothermia in procedures where viscera are exposed to the operating room environs over long periods of time.

A further object of the invention is to provide a surgical towel or drape effective to prevent patient body heat loss upon opening of major body cavities.

Another object of the invention is to provide a surgical towel capable of being wetted and applied to a surgical field, but which nonetheless avoids loss of body heat whether by radiation or by evaporation.

According to the invention, a surgical towel useful for avoiding accidental hypothermia, includes a body heat retaining layer portion of thermally insulative, flexible material, and a soft and absorbent covering layer portion fixed over at least one major surface of the body heat retaining layer. The body heat retaining layer and the covering layer portions together are capable of wrapping or draping about an organ that is exposed to the surrounding environs during an operation, thus preventing loss of body heat through the organ.

According to another aspect of the invention, a method of preventing hypothermia resulting from a surgical procedure during which organs are exposed, comprises arranging a thermally insulative flexible material between layers of soft absorbent surgical toweling, and wrapping an exposed organ with the surgical toweling containing the flexible insulative material thus preventing loss of body heat through the organ while the organ is exposed during the surgical procedure.

The various features of novelty that characterize the invention are pointed out with particularity by the claims annexed to and forming a part of the present disclosure. For a better understanding of the invention, its advantages and specific objects attained by its use, reference should be had to the accompanying drawing and descriptive matter in which there are illustrated and described preferred embodiments of the invention.

DETAILED DESCRIPTION OF THE INVENTION

Figure 1:
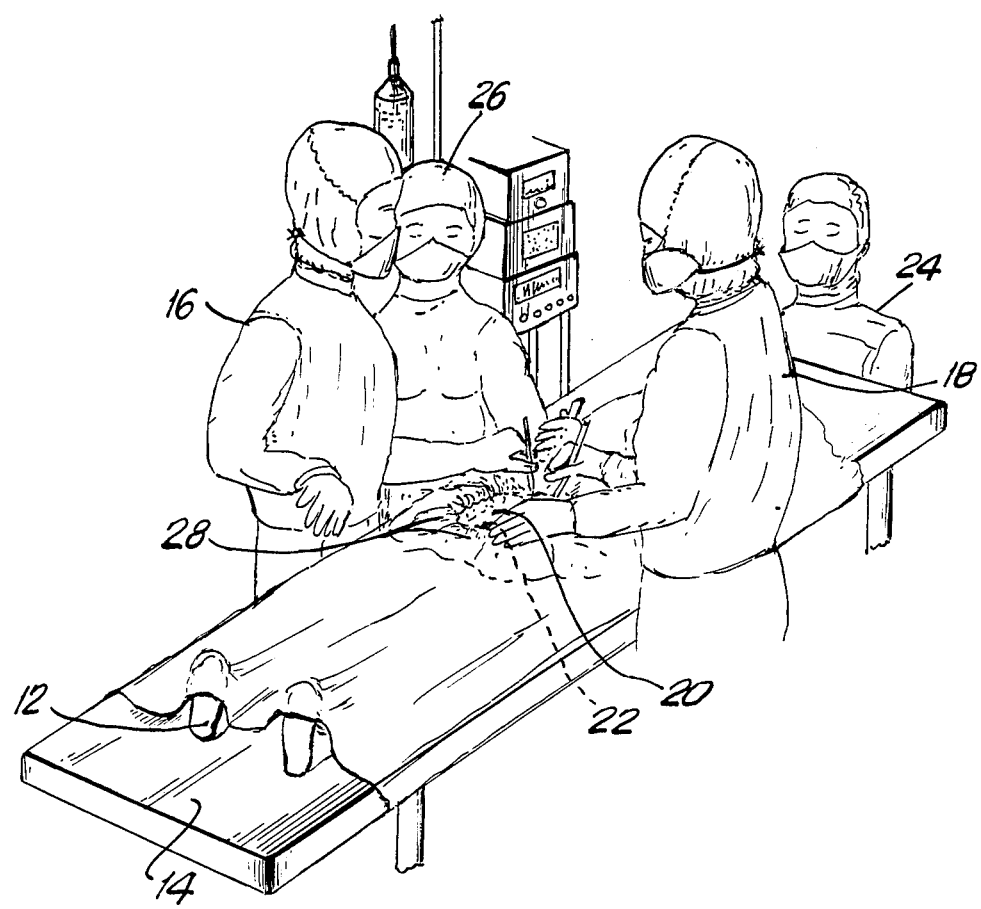
FIG. 1 is a view of an operating room showing an abdominal surgical procedure in progress.

FIG. 1 shows an operating room (OR) in which a patient 12 is undergoing an abdominal surgical procedure while lying on an operating table 14.

Figure 3:
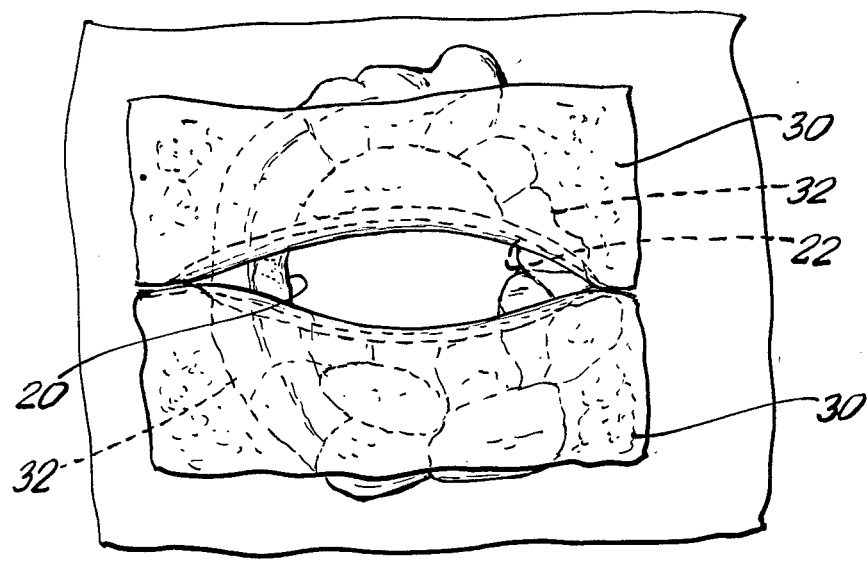
FIG. 3 is a top view of a surgical field including an abdominal incision exposing the patient's bowel, and with the present surgical toweling framing the incision.

Two surgeons 16, 18 on either side of the table 14 work with instruments inside a cavity 20 in the patient's abdomen, after making an incision 22 and exposing the patient's bowel (see FIG. 3). An anesthetist 24 works with appropriate equipment and monitoring devices at the patient's head end, while one or more nurses 26 assist the physicians.

Plain cotton towels 28 (sometimes called "blue towels") are ordinarily used to frame the incision 22, and are placed inside the abdominal cavity 20 (or other surgical field) to help wall off areas and to keep uninvolved organs out of the way. The towels 28 typically are kept wet and become icy cold. Even hospitals employing "all paper" disposable systems still rely on the cotton towels 28 for intra-operative use.

The patient's core body temperature thus will tend to decrease under the foregoing conditions because of heat loss (a) by radiation from the warm bowel, out of the cavity 20 and into the operating room environs which are usually maintained at 68° F.;

(b) by evaporation due to the application of the wet towels 28 directly on the patient's bowel and skin surrounding the incision 22;

(c) by conduction, i.e., direct contact between the patient's body and the cooler surface of operating table 14; and (d) by convection, i.e., circulation of cool air by OR air conditioning equipment over the region of the body cavity 20.

Patient body heat loss due to factors (c) and (d) is relatively slight when compared with factors (a) and (b) for surgical procedures that involve entering body cavities and exposing major organs. For example, see M. J. Goldberg, et al, Temperature Changes During Anesthesia and Operations, 93 Arch Surg 365, 368 (Aug. 1966).

It has been discovered that by arranging a thermally insulative material between layers of soft absorbent surgical toweling, and using the resultant composite to wrap or wall off an exposed organ, a patient will endure significantly less body heat loss when subjected to major abdominal or like kinds of surgery.

Figure 2:
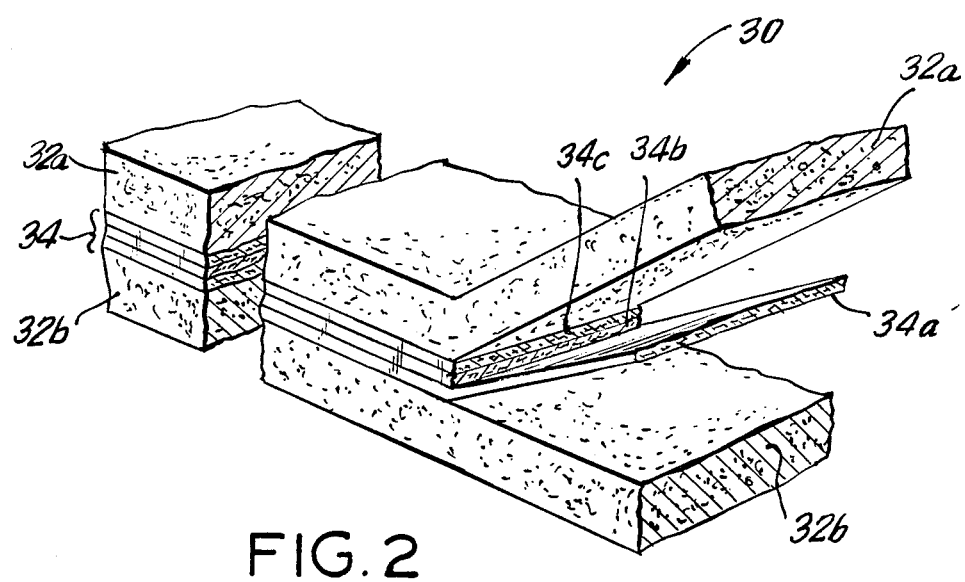
FIG. 2 is a partial sectional view of surgical toweling according to the invention.

FIG. 2 shows a first embodiment of composite surgical toweling 30 according to the invention. Soft and absorbent covering layers 32a, 32b are made from cotton or other suitable flexible material. The layers 32a, 32b are comprised of the conventional surgical "blue" towels. Each layer is typically about 1.5 mm thick when dry.

Sandwiched between the covering layers 32a, 32b is a body heat retaining layer portion 34 the major surfaces of which are bonded to the covering layers 32a, 32b with silicone adhesive. Body heat retaining layer 34 is made of thermally insulative flexible material. Preferably, the heat retaining layer 34 has the following characteristics:

1. Relatively thin but highly heat insulative;
2. Non-permeable;
3. Non-toxic; and
4. Non-flammable.

In the first embodiment, body heat retaining layer 34 is comprised of three layers 34a, 34b and 34c of "Space Blanket", each having a metallized film adhered on the major surfaces of a thin heat resistant cotton fibre layer. The three layers are bonded to one another with silicone adhesive, and together are about 1 mm thick. Each composite towel so constructed measures about 30 cm by 30 cm, with an overall thickness of about 4 mm.

Figure 4:
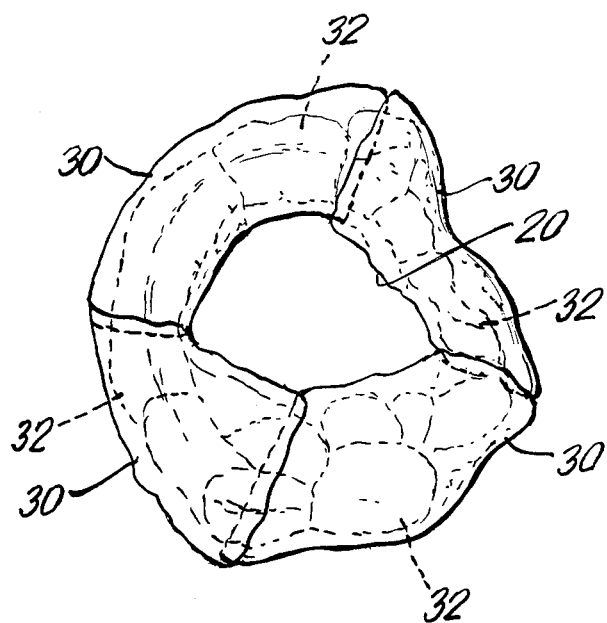
FIG. 4 is a view of the surgical field in FIG. 3 as seen below skin level, and with the present surgical toweling wrapping the exposed bowel.

In use, pieces of the toweling 30 frame parts of the incision 22 as shown in FIG. 3, and are applied inside the abdominal cavity 20 to wrap parts of organs 32 that are not being operated upon, as in FIG. 4. The covering layers 32a, 32b of the toweling 30 that contact the organs and the skin are kept wet to prevent drying of body tissue, as is done with the plain cotton towels 28 used before.

Comparative body heat retaining data was obtained for the first embodiment of the present toweling 30 and for the conventional towels 28, as follows:

EXAMPLE 1

A piece of conventional "blue towel" was evenly folded over a thermally insulative layer portion comprised of the three stacked layers of the mentioned Space Blanket material, and the layers were bonded with silicone adhesive to form a 30 cm by 30 cm piece of the first embodiment of toweling 30.

A length of flexible plastics tubing having an I.D. of 5 mm and a wall thickness of 1 mm, was arranged in a generally rectangular, meandering path about 100 inches long and fastened with clips against a flat wood board so as to simulate a patient's intestinal region inside the abdominal cavity 20. The tubing continued in a series path through a coiled portion immersed in a heated water bath, and through a pump. The tubing itself was filled with water and maintained liquid tight. A small desk fan was arranged to direct room air currents toward the simulated intestinal region.

Figure 5:
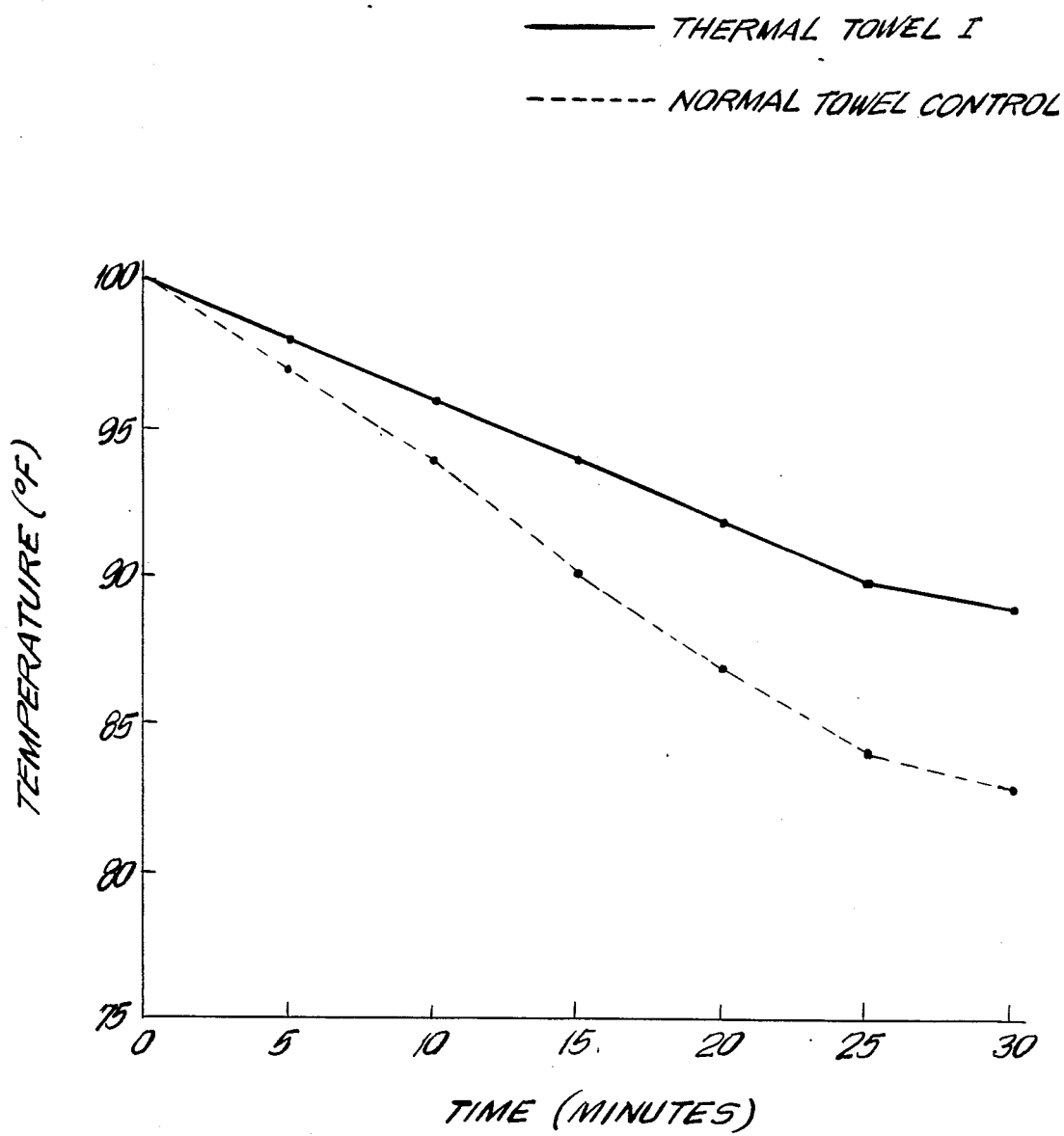
FIG. 5 is a graph showing body heat retaining characteristics of a first embodiment of the present surgical toweling as compared with a conventional cotton towel.

The water bath was contained by a foam insulated tank, and was pre-heated by an immersion heater. The heater was turned off when the water temperature reached 100° F. Water inside the tubing was thus heated as well. A folded piece of blue cotton towel acting as a control was thoroughly moistened and applied directly over the simulated intestinal region. The pump and the fan were then turned on, and the water bath temperature was monitored. The folded control towel was maintained wet as it would be during routine abdominal surgery. As shown in FIG. 5, the water bath temperature dropped from 100° F. to 83° F. over a 30 minute period.

The experiment was repeated using the present toweling 30 instead of the control towel. Both cotton outer layers of the toweling were kept wet over the 30 minute test run. FIG. 5 shows that for the same duration, the bath temperature decreased only to 89° F., i.e., 6° F. less temperature drop was achieved with the first embodiment of the toweling 30 as compared with the conventional towels 28 over a one-half hour period.

EXAMPLE 2

A second embodiment of the toweling 30 was made by substituting the three bonded layers of "Space Blanket" with a single layer of 0.125 (⅛) inch non-porous, closed-cell foam of the kind used for protective wrapping of fragile items, to provide the heat retaining layer 34. The single layer 34 was therefore light weight, relatively thin, malleable, and safe for patient and surgeon. Significantly, the single foam layer lacked any metallized coating or film as on the "Space Blanket" layers, thus making it safe from the influences of electrical fields or charge build-up during the course of an operation.

Figure 6:
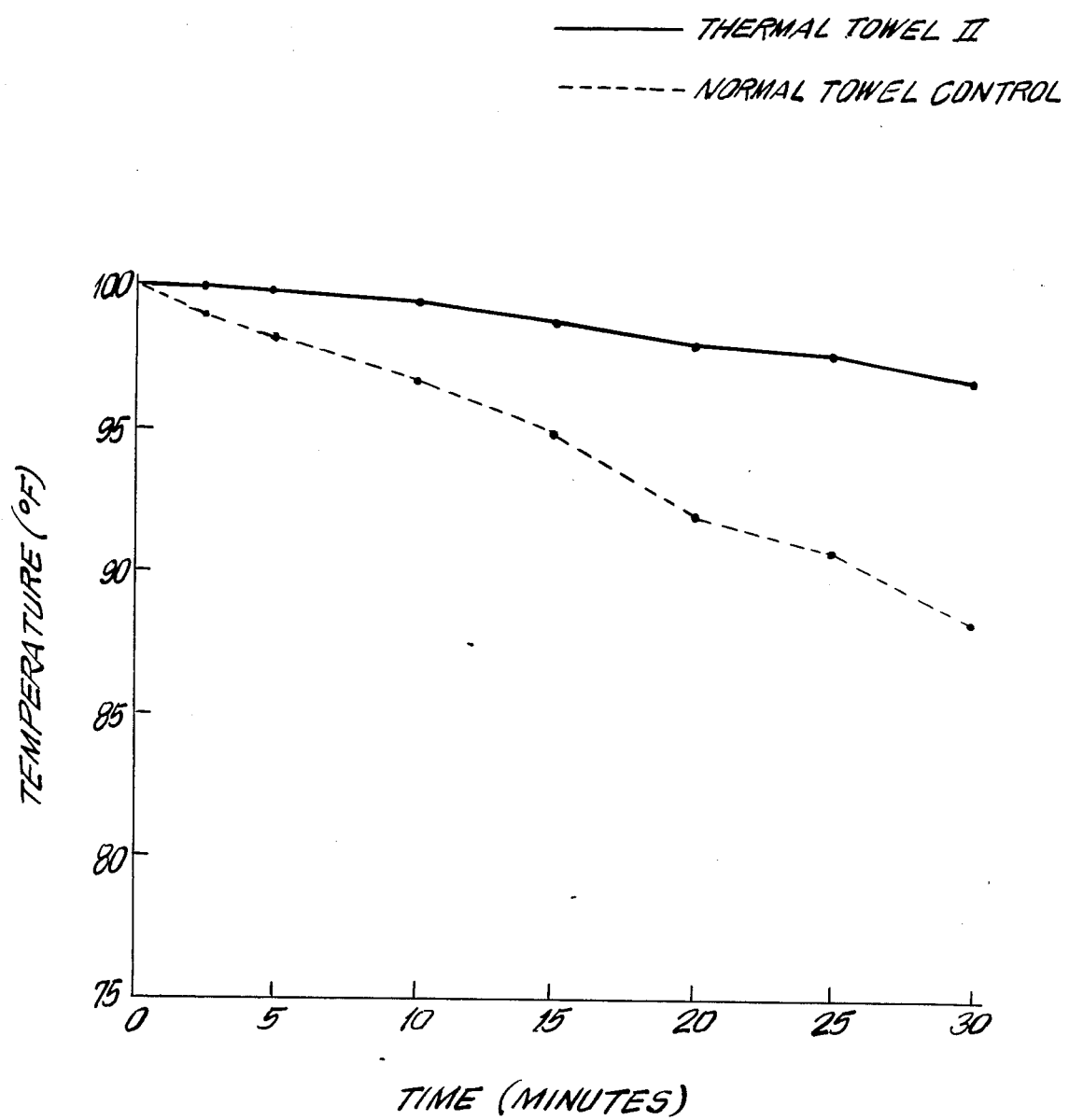
FIG. 6 is a graph similar to FIG. 5, showing comparative results when using a second embodiment of the present toweling.

FIG. 6 shows the results of an experiment conducted similarly to that in Example 1, but using the single ⅛ inch thick foam as heat retaining layer 34, instead of three plies of "Space Blanket". After 30 minutes, the tank water temperature was lowered by only about 3 degrees F. when using moist toweling with the single foam heat retaining layer 34, while over the same period of time the water temperature dropped 11 degrees F. with a conventional moist plain cotton towel. Thus, the toweling according to the second embodiment prevented the occurrence of an additional 8° F. temperature drop at the end of one-half hour.

While the foregoing description represents preferred embodiments of the present invention, it will be obvious to those skilled in the art that various changes and modifications may be made, without departing from the spirit and scope of the invention.

What is claimed is:

1. A method of preventing hypothermia resulting from a surgical procedure during which organs are exposed to the surrounding environs, comprising:
   bonding a thermally insulative flexible material to at least one layer of soft absorbent surgical toweling to form a thermally insulative towel;
   making an incision in a patient's body and defining an operating field in which organs are exposed to the surrounding environs; and
   maintaining a desirable level of patient core body heat during the surgical procedure by wrapping in situ an exposed organ with at least one thermally insulative towel and inhibiting heat transfer between the surface of the wrapped organ and the outside surface of the insulative towel;
   thereby preventing loss of the patient core body heat through the exposed organ and into the surrounding environs by the wrapping of the organ during the surgical procedure.

2. The method of claim 1, including framing a border of the operating field during the surgical procedure, with additional ones of the thermally insulative towel.

3. The method of claim 1, including placing a flexible vapor barrier between layers of the thermally insulative towel, and preventing patient body heat loss through said organ by evaporation.

4. The method of claim 1, including placing a flexible metallized film between layers of the thermally insulative towel, and preventing patient body heat loss through said organ by radiation.

5. The method of claim 1, including wetting the soft absorbent surgical toweling prior to wrapping of the exposed organ.

* * * * *